United States Patent
Bauer et al.

(10) Patent No.: US 7,838,580 B2
(45) Date of Patent: Nov. 23, 2010

(54) SALTS OF ALKYL ESTERS OF CARBOXYETHYL(ALKYL)PHOSPHINIC ACID

(75) Inventors: Harald Bauer, Kerpen (DE); Sebastian Hoerold, Diedorf (DE); Werner Krause, Huerth (DE)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 11/999,986

(22) Filed: Dec. 7, 2007

(65) Prior Publication Data

US 2008/0188598 A1    Aug. 7, 2008

(30) Foreign Application Priority Data

Dec. 12, 2006  (DE) ................. 10 2006 058 414

(51) Int. Cl.
    C08K 5/5313         (2006.01)
(52) U.S. Cl. ................. 524/126; 524/133; 588/153
(58) Field of Classification Search ................. 524/126, 524/133; 252/609; 588/153
    See application file for complete search history.

(56) References Cited

U.S. PATENT DOCUMENTS

| | | | |
|---|---|---|---|
| 6,555,227 B2 | 4/2003 | Sprenger et al. | |
| 6,753,363 B1 * | 6/2004 | Harashina | 524/99 |
| 7,485,745 B2 | 2/2009 | Mass et al. | |
| 2001/0014706 A1 | 8/2001 | Sprenger | |
| 2007/0155872 A1 * | 7/2007 | Hong et al. | 524/115 |
| 2007/0210288 A1 | 9/2007 | Mass et al. | |
| 2007/0213436 A1 | 9/2007 | Mass et al. | |
| 2007/0213563 A1 | 9/2007 | Mass et al. | |

FOREIGN PATENT DOCUMENTS

| | | |
|---|---|---|
| EP | 1125960 | 8/2001 |
| EP | 1832594 | 9/2007 |
| EP | 1832595 | 9/2007 |
| EP | 1832596 | 9/2007 |
| JP | 55 75425 * | 6/1980 |
| JP | 55 75425 A * | 6/1980 |
| JP | 2007070615 | 3/2007 |
| WO | WO 2006/090751 | 8/2006 |
| WO | WO 2007/007663 | 1/2007 |
| WO | WO 2007/011099 | 1/2007 |
| WO | WO 2007/007828 | 7/2007 |

OTHER PUBLICATIONS

European Search Report for EP 07023436, mailed Mar. 6, 2008.
Harashina Hatsuhiko "Fire-resistant Composition with Good Tracking Resistance," Caplus Jan. 19, 2007; XP 002433887.
English Abstract for JP 2007070615, Mar. 22, 2007.
English Abstract for WO 2007/007663. Jan. 18, 2007.

* cited by examiner

*Primary Examiner*—Peter Szekely
(74) *Attorney, Agent, or Firm*—Anthony A. Bisulca

(57) ABSTRACT

The invention relates to salts of alkyl esters of carboxyethyl (alkyl)phosphinic acid, where the salts have the formula (I)

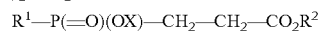

$R^1-P(=O)(OX)-CH_2-CH_2-CO_2R^2$ in which $R^1$ and $R^2$ are identical or different and, independently of one another, are
$C_1$-$C_{20}$-alkyl, $C_2$-$C_{20}$-alkenyl, $C_1$-$C_{20}$-alkynyl, and/or $C_6$-$C_{20}$-aralkyl, and
X is an alkali metal, an element of the second main and transition group, an element of the third main and transition group, an element of the fourth main and transition group, an element of the fifth main and transition group, an element of the sixth main group, an element of the seventh transition group, or an element of the eighth transition group, and also to processes for their preparation, and to their use.

33 Claims, No Drawings

SALTS OF ALKYL ESTERS OF CARBOXYETHYL(ALKYL)PHOSPHINIC ACID

The present invention is described in the German priority application No. 10 2006 058 414.7, filed 12 Dec. 2006, which is hereby incorporated by reference as is fully disclosed herein.

The invention relates to salts of alkyl esters of carboxyethyl (alkyl)phosphinic acid, to processes for their preparation, and to their use.

EP-A-1 125 960 describes latent combination compounds composed of epoxy resin hardeners and of flame retardants, and also describes latent ammonium salts obtainable from the reaction of said latent combination compounds with mono- or polyhydric hydroxy compounds. The latter can be used for the production of single-component resin systems and of moldings and coatings obtainable therefrom with flame-retardant properties, in hot-curable single-component epoxy resin adhesives, and with resin injection processes. EP-A-1 125 960 also encompasses prepregs and composite materials, and also printed circuit boards. Latent ammonium salts such as 1-methylimidazolium (2-methoxycarbonylethyl)(methyl) phosphinate are liquid at room temperature. They bond reactively as hardener or accelerator to the epoxy resin.

A disadvantage of the ammonium salts is the low thermal stability of the liquid substances, increasing the difficulty of processing in conventional plastics applications. Other disadvantageous effects are smoke generation during extrusion of the polymer molding compositions that are to be rendered flame-retardant, and the easy leaching of the compounds.

It is an object of the present invention to provide stable salts of alkyl esters of carboxyethyl(alkyl)phosphinic acid.

The invention therefore provides salts of alkyl esters of carboxyethyl(alkyl)phosphinic acid, where the salts have the formula (I)

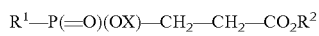

$R^1-P(=O)(OX)-CH_2-CH_2-CO_2R^2$ in which $R^1$ and $R^2$ are identical or different and, independently of one another, are
$C_1$-$C_{20}$-alkyl, $C_2$-$C_{20}$-alkenyl, $C_1$-$C_{20}$-alkynyl, and/or $C_6$-$C_{20}$-aralkyl, and X is an alkali metal, an element of the second main and transition group, an element of the third main and transition group, an element of the fourth main and transition group, an element of the fifth main and transition group, an element of the sixth main group, an element of the seventh transition group, or an element of the eighth transition group.

It is preferable that $R^1$ and $R^2$, identical or different, independently of one another, are H, methyl, ethyl, n-propyl, isopropyl, n-butyl, tert-butyl, n-pentyl, and/or phenyl.

It is preferable that X is Li, Na, K; Mg, Ca, Zn, Sr; Al, Ce, La; Ge, Sn, Pb, Ti, Zr; Sb, Bi; Cr, Mo, W; Mn; Fe, Co or Ni.

It is particularly preferable that X is H, Na, Al, Zn, Ca, Mg, Ti or Ce.

Another object of the present invention is to provide processes for the preparation of salts of alkyl esters of carboxyethyl(alkyl)phosphinic acid, of the formula (I).

This object is achieved via a process for the preparation of salts of alkyl esters of carboxyethyl(alkyl)phosphinic acid, of the formula (I), in which $R^1$, $R^2$ and X are defined as in claim 1, which comprises reacting an alkyl ester of carboxyethyl (alkyl)phosphinic acid, of the formula (I), in which $R^1$, $R^2$ are defined as in claim 1 and X is H, in a solvent system, with a reactant I, which is a compound of an alkali metal, of an element of the second main and transition group, of an element of the third main and transition group, of an element of the fourth main and transition group, of an element of the fifth main and transition group, of an element of the sixth transition group, of an element of the seventh transition group, or of an element of the eighth transition group.

The abovementioned object is also achieved via a process for the preparation of salts of alkyl esters of carboxyethyl (alkyl)phosphinic acid, of the formula (I), in which $R^1$, $R^2$ are defined as in claim 1, and X is an element of the second main and transition group, an element of the third main and transition group, an element of the fourth main and transition group, an element of the fifth main and transition group, an element of the sixth transition group, an element of the seventh transition group, or an element of the eighth transition group, which comprises reacting an alkali metal salt of alkyl esters of carboxyethyl(alkyl)phosphinic acid, of the formula (I), in which $R^1$, $R^2$ are defined as in claim 1 and X is an alkali metal, in a solvent system, with a reactant II.

It is preferable that the reactant II is borates, carbonates, hydroxides, oxides, oxide hydroxides, hydrogencarbonates, hydrogencarbonate hydrates, mixed hydrogencarbonates, mixed hydrogencarbonate hydrates, phosphates, sulfates, sulfate hydrates, hydrogensulfate hydrates, mixed hydrogensulfate hydrates, oxysulfates, acetates, nitrates, fluorides, fluoride hydrates, chloride, chloride hydrates, oxychlorides, bromides, iodides, iodide hydrates, or carboxylic acid derivatives, and/or alkoxides, of an element of the second main and transition group, of an element of the third main and transition group, of an element of the fourth main and transition group, of an element of the fifth main and transition group, of an element of the sixth transition group, of an element of the seventh transition group, or of an element of the eighth transition group.

The invention also provides the use of salts of alkyl esters of carboxyethyl(alkyl)phosphinic acid, of the formula (I), as flame retardant, in particular flame retardant for clear lacquers and intumescent coatings, flame retardant for wood and other cellulose-containing products, as reactive and/or non-reactive flame retardant for polymers, for the preparation of flame-retardant polymer molding compositions, for the production of flame-retardant polymer moldings, of flame-retardant polymer films, of flame-retardant polymer filaments, and of flame-retardant polymer fibers, and/or for providing flame retardancy to polyester and unblended or blended cellulose textiles via impregnation.

The invention likewise provides the use of salts of alkyl esters of carboxyethyl(alkyl)phosphinic acid, of the formula (I), as binders for foundry materials or molding sands; as crosslinking agent or accelerators in the hardening of epoxy resins, of polyurethanes, and of unsaturated polyester resins;

as polymer stabilizers, for example as light stabilizer, free-radical scavenger, and/or heat stabilizers for cotton textiles, polymer fibers, plastics;

as plant-protection agents, for example as plant-growth regulator, or as herbicide, pesticide or fungicide;

as therapeutic agent or additive in therapeutic agents for humans and animals, e.g. as enzyme modulator, for stimulation of tissue growth;

as sequestering agent, e.g. for the control of deposits in industrial water supply systems, in petroleum production, and in a metal-treatment composition;

as petroleum additive, e.g. as antioxidant, and for increasing octane number; or as corrosion-protection agent;

in laundry-detergent and cleaning-product applications, e.g. as decolorizer;

in electronics applications, e.g. in polyelectrolytes for capacitors, batteries, and accumulators, or else as free-radical scavenger in photosensitive layers;

or as aldehyde scavenger;

or as formaldehyde scavenger in adhesive compositions and moldings, e.g. in construction applications, in the automobile industry, in ship building, in the aerospace industry, and for electrical engineering.

The invention also provides a flame-retardant thermoplastic polymer molding composition comprising from 0.5 to 45% by weight of salts of alkyl esters of carboxyethyl(alkyl)phosphinic acid, of the formula (I), as claimed in at least one of claims 1 to 4, and from 0.5 to 99.5% by weight of thermoplastic polymer or a mixture of these, where the entirety of the components is 100% by weight.

The thermoplastic polymers of the flame-retardant thermoplastic polymer molding composition are preferably polymers of mono- and diolefins, e.g. polyethylene, polypropylene, polyisobutylene, poly-1-butene, poly-4-methyl-1-pentene, polyisoprene, or polybutadiene, or else polymers of cycloolefins, e.g. of cyclopentene or norbornene; polyvinyl chloride, polyvinylidene chloride, polyvinyl fluoride, polyvinylidene fluoride; polyacrylates and polymethacrylates, polyacrylamides, polyacrylonitriles, polyvinyl alcohol, polyvinyl acetate, polyalkylene glycols, polyethylene oxide, polypropylene oxide, polyoxymethylene, polyphenylene oxides and polyphenylene sulfides, polyphenylene ether, polyurethanes, polyamides, and copolyamides, polyureas, polyimides, polyamideimides, polyetherimides, polyesterimides, polyhydantoins, and polybenzimidazoles; or polyesters, such as polyethylene terephthalate or polybutylene terephthalate.

The invention also provides a flame-retardant thermoset composition, comprising from 0.1 to 45% by weight of salts of alkyl esters of carboxyethyl(alkyl)phosphinic acid, of the formula (I), as claimed in at least one of claims 1 to 4, from 40 to 89.9% by weight of unsaturated polyesters, and from 10 to 60% by weight of vinyl monomer, where the entirety of the components is 100% by weight.

A process for the preparation of flame-retardant polymer molding compositions comprises mixing the salts of alkyl esters of carboxyethyl(alkyl)phosphinic acid, of the formula (I), with polymer pellets and optionally with additives, and incorporating them in a twin-screw extruder at temperatures of about 170° C. (polystyrene), about 270° C. (PET, polyethylene terephthalate), from 230 to 260° C. (polybutylene terephthalate, PBT), of about 260° C. (PA6) or of from 260 to 280° C. (PA 66), and then drawing off the homogenized polymer strand, cooling it in a water bath, and then pelletizing it and drying it to a residual moisture content of from 0.05 to 5%, preferably from 0.1 to 1% by weight.

The invention also provides a flame-retardant molding composition, comprising from 0.5 to 50% by weight of salts of alkyl esters of carboxyethyl(alkyl)phosphinic acid, of the formula (I), as claimed in at least one of claims 1 to 4, from 5 to 99.5% by weight of an epoxy resin, and from 0 to 20% by weight of a hardener, where the entirety of the components is 100% by weight.

The abovementioned flame-retardant molding compositions are preferably used for the production of flame-retardant polymer moldings, of flame-retardant polymer films, of flame-retardant polymer filaments, or of flame-retardant polymer fibers.

The invention also encompasses mixtures, comprising from 0.1 to 99.9% by weight of salts of alkyl esters of carboxyethyl(alkyl)phosphinic acid, of the formula (I), and from 0.1 to 99.9% by weight of salts of alkyl esters of carboxyethyl(alkyl)phosphinic acid, of the formula (II)

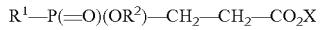

where $R^1$, $R^2$ and X are defined as in claim 1.

It is preferable that said mixtures are used for the preparation of flame-retardant polymer molding compositions and for the production of flame-retardant polymer moldings, of flame-retardant polymer films, of flame-retardant polymer filaments, or of flame-retardant polymer fibers.

Finally, the invention also provides a process for the production of flame-retardant polymer moldings, which comprises processing an abovementioned flame-retardant molding composition or a mixture composed of salts of alkyl esters of carboxyethyl(alkyl)phosphinic acid, of the formula (I) and (II), in the form of a flame-retardant molding composition, using an injection-molding machine, at melt temperatures of from 200 to 250° C. in the case of polystyrene, from 200 to 300° C. in the case of polypropylene, from 250 to 290° C. in the case of polyethylene terephthalate (PET), from 230 to 270° C. in the case of polybutylene terephthalate (PBT), from 260 to 290° C. in the case of nylon-6 (PA 6), from 260 to 290° C. in the case of nylon-6,6 (PA 6.6), or from 280 to 320° C. in the case of polycarbonate, to give polymer moldings.

It is preferable that the groups $R^1$ and $R^2$ are linear, branched, or cyclic, part of a ring system, bear heteroatoms, and/or bear a functional group. Preferred functional groups are carbonyl, aldehyde, carboxy, hydroxy, sulfonic acid, nitrile, cyano, epoxy, and primary, secondary, and/or tertiary amino groups, and/or unsubstituted, partially substituted, or fully substituted triazines. Preferred alkyl groups are $C_1$-$C_8$-alkyl, and preferably methyl, ethyl, n-propyl, isopropyl, n-butyl, sec-butyl, tert-butyl, n-octyl, and ethylhexyl. Preferred carboxyalkyl groups are those of $(CH_2)_n CO_2 H$ type, where n=from 1 to 6. Preferred hydroxyalkyl groups are of $(CH_2)_n OH$ type, where n=from 1 to 6.

It is preferable that the inventive salt of alkyl esters of carboxyethyl(alkyl)phosphinic acid is type (I), where $R^1$ is methyl and $R^2$ is methyl, e.g: $H_3C$—$P(=O)(ONa)$—$CH_2$—$CH_2$—$CO_2CH_3$$H_3C$—$P(=O)(OMg_{1/2})$—$CH_2$—$CH_2$—$CO_2CH_3$$H_3C$—$P(=O)(OCa_{1/2})$—$CH_2$—$CH_2$—$CO_2CH_3$$H_3C$—$P(=O)(OZn_{1/2})$—$CH_2$—$CH_2$—$CO_2CH_3$$H_3C$—$P(=O)(OAl_{1/3})$—$CH_2$—$CH_2$—$CO_2CH_3$$H_3C$—$P(=O)(OTi_{1/3})$—$CH_2$—$CH_2$—$CO_2CH_3$$H_3C$—$P(=O)(OCe_{1/3})$—$CH_2$—$CH_2$—$CO_2CH_3$$H_3C$—$P(=O)(OFe_{1/3})$—$CH_2$—$CH_2$—$CO_2CH_3$.

It is also preferable that the inventive salt of alkyl esters of carboxyethyl(alkyl)phosphinic acid is of type (I), where $R^1$ is ethyl and $R^2$ is methyl, e.g.: $H_3C$—$CH_2$—$P(=O)(ONa)$—$CH_2$—$CH_2$—$CO_2CH_3$$H_3C$—$CH_2$—$P(=O)(OMg_{1/2})$—$CH_2$—$CH_2$—$CO_2CH_3$$H_3C$—$CH_2$—$P(=O)(OZn_{1/2})$—$CH_2$—$CH_2$—$CO_2CH_3$$H_3C$—$CH_2$—$P(=O)(OAl_{1/3})$—$CH_2$—$CH_2$—$CO_2CH_3$$H_3C$—$CH_2$—$P(=O)(OTi_{1/3})$—$CH_2$—$CH_2$—$CO_2CH_3$.

It is also preferable that the inventive salt of alkyl esters of carboxyethyl(alkyl)phosphinic acid is of type (I), where $R^1$ is methyl and $R^2$ is octyl, e.g.: $H_3C$—$P(=O)(ONa)$—$CH_2$—$CH_2$—$CO_2C_8H_{17}$$H_3C$—$P(=O)(OMg_{1/2})$—$CH_2$—$CH_2$—$CO_2C_8H_{17}$$H_3C$—$P(=O)(OZn_{1/2})$—$CH_2$—$CH_2$—

$CO_2C_8H_{17}H_3C-P(=O)(OAl_{1/3})-CH_2-CH_2-CO_2C_8H_{17}H_3C-P(=O)(OTi_{1/3})-CH_2-CH_2-CO_2C_8H_{17}$.

In another embodiment, the inventive salt is of type (II)

$$R^1-P(=O)(OR^2)-CH_2-CH_2-CO_2X$$

where $R^1$, $R^2$, and X are defined as in formula (I).

It is preferable that the inventive salt of alkyl esters of carboxyethyl(alkyl)phosphinic acid is of type (II), where $R^1$ is methyl and $R^2$ is methyl, e.g.: $H_3C-P(=O)(OCH_3)-CH_2-CH_2-CO_2Na$  $H_3C-P(=O)(OCH_3)-CH_2-CH_2-CO_2Ca_{1/2}H_3C-P(=O)(OCH_3)-CH_2-CH_2-CO_2Al_{1/3}H_3C-P(=O)(OCH_3)-CH_2-CH_2-CO_2Ti_{1/3}$  $H_3C-P(=O)(OCH_3)-CH_2-CH_2-CO_2Fe_{1/3}$.

In another embodiment, preference is given to partial hydroxides of type III:

$$[R^1-P(=O)(OX)-CH_2-CH_2-CO_2R^2]_{1-y}(OH)_y,$$

where y is from 0 to less than or equal to 1.

It is preferable that the inventive salt of alkyl esters of carboxyethyl(alkyl)phosphinic acid is of type (III), where $R^1$ is methyl and $R^2$ is methyl, e.g.: $[H_3C-P(=O)(OAl_{1/3})-CH_2-CH_2-CO_2CH_3]_{1-y}(OH)_y$.

In another embodiment, preference is given to partial hydroxides of type IV:

$$[R^1-P(=O)(OR^2)-CH_2-CH_2-CO_2X]_{1-y}(OH)_y,$$

where y is from 0 to less than or equal to 1.

It is preferable that the inventive salt of alkyl esters of carboxyethyl(alkyl)phosphinic acid is of type (IV), where $R^1$ is methyl and $R^2$ is methyl, e.g.: $[H_3C-P(=O)(OCH_3)-CH_2-CH_2-CO_2Ca_{1/2}]_{1-y}(OH)_y$.

It is preferable that the residual moisture levels of the salts of alkyl esters of carboxyethyl(alkyl)phosphinic acid, of type (I) to (IV) are from 0.01 to 10% by weight, in particular from 0.1 to 1% by weight.

It is preferable that the average particle sizes of the salts of alkyl esters of carboxyethyl(alkyl)phosphinic acid, of type (I) to (IV) are from 0.1 to 2000 μm, in particular from 10 to 500 μm.

It is preferable that the bulk densities of the salts of alkyl esters of carboxyethyl(alkyl)phosphinic acid, of type (I) to (IV) are from 80 to 1200 g/l, in particular from 150 to 800 g/l.

It is preferable that the decomposition temperatures in the air of the salts of alkyl esters of carboxyethyl(alkyl)phosphinic acid, of type (I) to (IV) are from 250 to 350° C., in particular from 280 to 340° C.

It is preferable that the BET surface areas of the salts of alkyl esters of carboxyethyl(alkyl)phosphinic acid, of type (I) to (IV) are from 1 to 100 m$^2$/g, in particular from 2 to 20 m$^2$/g.

It is preferable that the room-temperature solubilities of the salts of alkyl esters of carboxyethyl(alkyl)phosphinic acid, of type (I) to (IV) are from 0.1 to 50 g/100 ml of water, in particular from 0.5 to 20 g/100 ml of water.

The abovementioned salts of alkyl esters of carboxyethyl(alkyl)phosphinic acid can be prepared by various processes.

One process (1) for the preparation of alkyl esters of carboxyethyl(alkyl)phosphinic acid comprises reacting a derivative of a carboxyethyl(alkyl)phosphinic acid in an esterification reaction with an alcohol to give an alkyl ester of carboxyethyl(alkyl)phosphinic acid.

A preferred derivative of a phosphinic acid is provided by phosphinic acids themselves, phosphinyl chlorides, phosphinic anhydrides, e.g. 3-(hydroxymethylphosphinyl)propionic acid $H_3C-P(O)(OH)CH_2-CH_2-CO_2H$, 2-methyl-1,2-oxaphospholan-5-one 2-oxide, cyclo($-P(=O)(CH_3)-CH_2-CH_2-CO_2-$), 2-ethyl-1,2-oxaphospholan-5-one 2-oxide, methyl(2-chlorocarbonylethyl)phosphinyl chloride, and 3-(chloromethylphosphinyl)propionyl chloride, $H_3C-P(O)(Cl)CH_2-CH_2-COCl$.

Preferred alcohols are methanol, ethanol, isopropanol, n-propanol, n-butanol, isobutanol, tert-butanol, n-amyl alcohol, isoamyl alcohol, tert-amyl alcohol, n-hexanol, n-octanol, isooctanol, n-tridecanol, benzyl alcohol, etc.

For the preparation process (1) a solvent can be used, and preference is given to water, alcohols; and aliphatic hydrocarbons, such as pentane, hexane, heptane, octane, and petroleum ether, naphtha, kerosene, petroleum, paraffin oil, etc.; aromatic hydrocarbons, such as benzene, toluene, xylene, mesitylene, ethylbenzene, diethylbenzene, etc.; halogenated hydrocarbons, such as methylene chloride, chloroform, 1,2-dichloroethane, chlorobenzene, carbon tetrachloride, tetrabromoethylene, etc.; alicyclic hydrocarbons, such as cyclopentane, cyclohexane, and methylcyclohexane, etc.; ethers, such as anisole (methyl phenyl ether), tert-butyl methyl ether, dibenzyl ether, diethyl ether, dioxane, diphenyl ether, methyl vinyl ether, tetrahydrofuran, triisopropyl ether etc.; glycol ethers, such as diethylene glycol diethyl ether, diethylene glycol dimethyl ether (diglyme), diethylene glycol monobutyl ether, diethylene glycol monomethyl ether, 1,2-dimethoxyethane (DME, monoglyme), ethylene glycol monobutyl ether, triethylene glycol dimethyl ether (triglyme), triethylene glycol monomethyl ether etc.; ketones, such as acetone, diisobutyl ketone, methyl n-propyl ketone; methyl ethyl ketone, methyl isobutyl ketone, etc.

In process (1), preference is given to a ratio of solvent to alkyl ester of carboxyethyl(alkyl)phosphinic acid of from 100:1 to 1:100 parts by weight, particularly from 10:1 to 1:10.

In process (1), preference is given to a ratio of alcohol to alkyl ester of carboxyethyl(alkyl)phosphinic acid of from 100:1 to 1:10 mol/mol, particularly from 15:1 to 1:1 mol/mol.

In process (1), preference is given to a reaction time of from 0.1 to 100 h, particularly preferably from 1 to 10 h.

In process (1), preference is given to a pH of from 1 to 5, particularly preferably from 1.4 to 2.

Preferred temperature for the formation process in process (1) is from −20 to 300° C., particularly preferably from 0 to 80° C.

Preferred pressure for the formation process in process (1) is from 10 to 100 000 000 Pa.

Preferred reactant I is a salt of an element of the first main group, preferably an alkali metal hydroxide, alkali metal oxide hydroxide, alkali metal hydroxide carbonate, alkali metal hydrogencarbonate, alkali metal carbonate, alkali metal alcoholate, particular preference being given to lithium hydroxide, sodium hydroxide, potassium hydroxide, sodium carbonate, potassium carbonate, potassium hydrogencarbonate, sodium hydrogencarbonate, trona, or aqueous solutions thereof; sodium methoxide, sodium ethoxide, sodium n-propoxide, sodium isopropoxide, sodium n-butoxide, sodium isobutoxide, sodium tert-butoxide, sodium amyl alcoholate, or sodium glycolate.

Another preferred reactant I is a salt of an element of the second main and transition group, preferably alkaline earth metal hydroxide, alkaline earth metal oxide hydroxide, alkaline earth metal hydroxide carbonate, in particular magnesium hydroxide (Magnifin® H5, Albemarle), hydrotalcite ($Mg_6Al_2(OH)_{16}CO_3$*n $H_2O$), dihydrotalcite, magnesium carbonates, or magnesium calcium carbonates, calcium hydroxide, basic zinc carbonate, zinc hydroxide carbonate, basic zinc carbonate hydrate, zinc hydroxides, or mixed zinc oxide hydroxides (standard zinc oxide, G6 zinc white, 2011 zinc oxide, F-80 zinc oxide, Pharma 8® zinc white, Pharma A® zinc white, Rotsiegel® zinc white, Weissiegel® zinc white from Grillo-Werke AG, activated zinc oxide, e.g. from Rheinchemie, zincite, calamine), or tert-hydroxystannate.

Another preferred component I is a salt of an element of the third main and transition group, preferably aluminum hydroxide, cerium hydroxide, lanthanum hydroxide, aluminum alcoholate, cerium alcoholate, lanthanum alcoholate, aluminum hydroxide, or mixed aluminum oxide hydroxide, dihydroxyaluminum sodium carbonate ($NaAl(OH)_2CO_3$), and/or polyaluminum hydroxy compounds, which preferably have from 9 to 40% by weight aluminum content.

Preference is given to a pH of from 4 to 9, particularly from 6 to 8.5.

Another preferred component I is a salt of an element of the fourth main and transition group, preferably tin hydroxides, lead hydroxides, titanium oxide hydroxides, zirconium oxide hydroxides, tin alcoholates, titanium alcoholates, and zirconium alcoholates.

Preferred titanium alcoholates, i.e. titanium alkoxides, are titanium(IV) n-propoxide (Tilcom® NPT, Vertec® NPT), titanium(IV) n-butoxide, titanium chloride triisopropoxide, titanium(IV) ethoxide, or titanium(IV) 2-ethylhexoxide (Tilcom® EHT, Vertetec® EHT).

Preferred tin alcoholate (tin alkoxide) is tin(IV) tert-butoxide.

Preferred zirconium alcoholate, i.e. zirconium alkoxide, is zirconium(IV) tert-butoxide.

Preferred reactants II are aluminum chloride, aluminum nitrate, aluminum sulfate, cerium(III) nitrate, iron(III) sulfate, titanyl sulfate, zinc nitrate, zinc sulfate and/or zinc chloride.

Preference is given to a pH of from 1 to 8, in particular from 2.5 to 6.

The reaction is preferably carried out in a solvent system.

It is preferable that the reaction is carried out by the process as claimed in claims 5 to 7, where the solids content of the inventive salts of alkyl esters of carboxyethyl(alkyl)phosphinic acid is from 0.1 to 70% by weight, preferably from 5 to 40% by weight.

The reaction in the process as claimed in claims 5 to 7 is preferably carried out at a temperature of from –20 to +500° C., particularly from 50 to 120° C.

It is preferable that the ratio of component I and, respectively, II to the phosphorus (of the inventive (salts of) alkyl esters of carboxyethyl(alkyl)phosphinic acid) in the process as claimed in claims 5 to 7 is from 0.8 to 3 ion equivalent (mol per cation charge), particularly preferably from 1 to 2 ion equivalent.

It is preferable that the ratio of solvent to the phosphorus (of the inventive (salts of) alkyl esters of carboxyethyl(alkyl) phosphinic acid) in the process as claimed in claims 5 to 7 is from 2 to 1000 mol/mol, particularly from 4 to 100 mol/mol.

It is preferable that the reaction time in the process as claimed in claims 5 to 7 is from 0.1 to 100, particularly preferably from 1 to 10 h.

Preferred temperature for the formation process in the process as claimed in claims 5 to 7 is from 20 to 300° C., particularly from 50 to 200° C.

Preferred pressure for the formation process in the process as claimed in claims 5 to 7 is from 10 to 100 000 000 Pa.

It is preferable that the reaction takes place in the process as claimed in claims 5 to 7 in a stirred tank, mixer and/or kneader.

It is preferable that the reaction in the process as claimed in claims 5 to 7 is carried out with energy input of from 0.083 to 1.65 $kW/m^3$, particularly from 0.33 to 1.65 $kW/m^3$.

It is preferable that the inventive salts of alkyl esters of carboxyethyl(alkyl)phosphinic acid in the process as claimed in claims 5 to 7 are isolated from the reaction mixture via filtration and/or centrifuging.

It is preferable that the inventive salts of alkyl esters of carboxyethyl(alkyl)phosphinic acid in the process as claimed in claims 5 to 7 are isolated using pressure filter funnels, vacuum filter funnels, filter funnels with stirrer, pressure rise candle filters, axial leaf filters, circular leaf filters, centrifugal leaf filters, chamber-frame filter presses, automatic chamber filter presses, vacuum multicompartment drum filters, vacuum multicompartment leaf filters, vacuum horizontal-table filters, side-feed vacuum filters, rotation pressure filters, or vacuum belt filters.

It is preferable that the filtration pressure in the process as claimed in claims 5 to 7 is from 0.5 Pa to 6 MPa.

It is preferable that the filtration temperature in the process as claimed in claims 5 to 7 is from 0 to 400° C.

It is preferable that the specific filter performance in the process as claimed in claims 5 to 7 is from 10 to 200 $kg*h^{-1}*m^{-2}$.

It is preferable that the residual moisture level of the filter cake in the process as claimed in claims 5 to 7 is from 5 to 60%.

It is preferable that the inventive salts of alkyl esters of carboxyethyl(alkyl)phosphinic acid in the process as claimed in claims 5 to 7 are isolated using solid-wall centrifuges, such as overflow centrifuges, plow centrifuges, chamber centrifuges, helical-conveyor centrifuges, disk centrifuges, tube centrifuges, sieve centrifuges, such as overdriven centrifuges and underdriven centrifuges, screen-conveyor centrifuges, screen-plough centrifuges, or reciprocating-conveyor centrifuges.

It is preferable that the acceleration ratio in the process as claimed in claims 5 to 7 is from 300 to 15 000.

It is preferable that the suspension throughput rate in the process as claimed in claims 5 to 7 is from 2 to 400 $m^3*h^{-1}$.

It is preferable that the solids throughput rate in the process as claimed in claims 5 to 7 is from 5 to 80 $t*h^{-1}$.

It is preferable that the residual moisture level of the cake in the process as claimed in claims 5 to 7 is from 5 to 60%.

It is preferable that the salts of inventive salts of alkyl esters of carboxyethyl(alkyl)phosphinic acid in the process as claimed in claims 5 to 7 are dried.

Suitable assemblies for the drying in the process as claimed in claims 5 to 7 are chamber dryers, channel dryers, belt dryers (air velocity from 2 to 3 m/s), disk dryers (temperature from 20 to 400° C.), drum dryers (hot gas temperature from 100 to 250° C.), paddle dryers (temperature from 50 to 300° C.), pneumatic dryers (air velocity from 10-60 m/s, exhaust air temperature from 50 to 300° C.), fluidized-bed dryers (air velocity from 0.2 to 0.5 m/s, exhaust air temperature from 50 to 300° C.), cylinder dryers, tubular dryers (temperature from 20 to 200° C.), paddle dryers, vacuum drying cabinets (temperature from 20 to 300° C., pressure from 0.001 to 0.016 MPa), vacuum-drum dryers (temperature from 20 to 300° C., pressure from 0.004 to 0.014 MPa), vacuum paddle dryers (temperature from 20 to 300° C., pressure from 0.003 to 0.02 MPa), vacuum conical dryers (temperature from 20 to 300° C., pressure from 0.003 to 0.02 MPa).

The invention also provides the use of salts of alkyl esters of carboxyethyl(alkyl)phosphinic acid, of type (I) or (II), or a mixture thereof, as flame retardants.

The invention also provides for the use of the inventive salts of alkyl esters of carboxyethyl(alkyl)phosphinic acid, (I) or (II), or a mixture thereof, in flame retardants. The inventive salts of alkyl esters of carboxyethyl(alkyl)phosphinic acid are less readily dissolved out of the flame-retardant molding compositions, and also have flame-retardant activity at substantially lower temperatures than representatives of the prior art.

The invention also provides a flame-retardant thermoset polymer molding composition, comprising from 0.1 to 45% by weight of salts of alkyl esters of carboxyethyl(alkyl)phosphinic acid, of type (I) or (II), or a mixture thereof, from 15 to 80% by weight of polystyrene-based polymer and from 15 to 80% by weight of polyphenylene ether, where the entirety of the components is 100% by weight.

The invention also provides a flame-retardant epoxy resin, comprising from 0.5 to 50% by weight of salts of alkyl esters of carboxyethyl(alkyl)phosphinic acid of type (I) or (II), or a mixture thereof, from 5 to 99.5% by weight of an epoxy resin and from 0 to 20% by weight of a hardener, wherein the entirety of the components is 100% by weight.

Preference is given to a process for the preparation of flame-retardant polymer molding compositions, which comprises mixing the inventive salts of alkyl esters of carboxyethyl(alkyl)phosphinic acid with the polymer pellets and optionally with additives, and incorporating them in a twin-screw extruder (ZSK 25 WLE, 14.5 kg/h, 200 rpm, L/D:4) at temperatures of 170° C. (polystyrene), about 270° C. (PET, polyethylene terephthalate), from 230 to 260° C. (polybutylene terephthalate, PBT), of 260° C. (PA6) or of from 260 to 280° C. (PA 66). The homogenized polymer strand is drawn off, cooled in a water bath, and then pelletized and dried to a residual moisture content of from 0.05 to 5%, preferably from 0.1 to 1% by weight.

Preference is given to a process for preparation of a flame-retardant polymer molding composition which comprises polymerizing 1000 parts by weight of dimethyl terephthalate and 720 parts by weight of ethylene glycol, and from 35 to 700 parts by weight of inventive salt of alkyl esters of carboxyethyl(alkyl)phosphinic acid. Optionally, the polymerization reaction can be carried out in the presence of zinc acetate. Optionally, the flame-retardant polymer molding composition can be spun to give fibers.

The polymer is preferably a thermoplastic or thermoset polymer.

The thermoplastic polymers are preferably polymers of mono- and diolefins, e.g. polypropylene, polyisobutylene, poly-1-butene, poly-4-methyl-1-pentene, polyisoprene, or polybutadiene, or else polymers of cycloolefins, e.g. of cyclopentene or norbornene; or polyethylene (which may optionally have been crosslinked), e.g. high-density polyethylene (HDPE), high-density high-molecular-weight polyethylene (HDHMWPE), high-density ultrahigh-molecular-weight polyethylene (HDUHMWPE), medium-density polyethylene (MDPE), low-density polyethylene (LDPE), linear low-density polyethylene (LLDPE), branched low-density polyethylene (VLDPE), or else a mixture thereof.

It is preferable that the thermoplastic polymers are copolymers of mono- and diolefins with one another or with other vinyl monomers, e.g. ethylene-propylene copolymers, linear low-density polyethylene (LLDPE), or a mixture of this with low-density polyethylene (LDPE), propylene-1-butene copolymers, propylene-isobutylene copolymers, ethylene-1-butene copolymers, ethylene-hexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers and their copolymers with carbon monoxide, or ethylene-acrylic acid copolymers and their salts (ionomers), or else terpolymers of ethylene with propylene and with a diene, such as hexadiene, dicyclopentadiene, or ethylidenenorbornene; or a mixture of these copolymers with one another, e.g. polypropylene/ethylene-propylene copolymers, LDPE/ethylene-vinyl acetate copolymers, LDPE/ethylene-acrylic acid copolymers, LLDPE/ethylene-vinyl acetate copolymers, LLDPE/ethylene-acrylic acid copolymers, and alternating or random-structure polyalkylene/carbon monoxide copolymers, or a mixture of these with other polymers, e.g. with polyamides.

It is preferable that the polymers are hydrocarbon resins (e.g. $C_5$-$C_9$) inclusive of hydrogenated modifications thereof (e.g. tackifier resins), and mixtures of polyalkylenes and starch.

It is preferable that the thermoplastic polymers are polystyrene, poly(p-methylstyrene), and/or poly(alpha-methylstyrene).

It is preferable that the thermoplastic polymers are copolymers of styrene or alpha-methylstyrene with dienes or with acrylic derivatives, e.g. styrene-butadiene, styrene-acrylonitrile, styrene-alkyl methacrylate, styrene-butadiene-alkyl acrylate and the corresponding methacrylate, styrene-maleic anhydride, styrene-acrylonitrile-methyl acrylate; a mixture of high impact resistance composed of styrene copolymers and of another polymer, e.g. of a polyacrylate, of a diene polymer, or of an ethylene-propylene-diene terpolymer; or else block copolymers of styrene, e.g. styrene-butadiene-styrene, styrene-isoprene-styrene, styrene-ethylene/butylene-styrene, or styrene-ethylene/propylene-styrene.

It is preferable that the thermoplastic polymers are graft copolymers of styrene or alpha-methylstyrene, e.g. styrene on polybutadiene, styrene on polybutadiene-styrene copolymers or on polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates and, respectively, alkyl methacrylates on polybutadiene, styrene and acrylonitrile on ethylene-propylene-diene terpolymers, styrene and acrylonitrile on polyalkyl acrylates or on polyalkyl methacrylates, styrene and acrylonitrile on acrylate-butadiene copolymers, or else a mixture of these, for example that known as ABS polymer, MBS polymer, ASA polymer, or AES polymer.

It is preferable that the polystyrene-based polymers are blends composed of a) from 3 to 30% by weight, particularly preferably from 1 to 15% by weight, of elastomers based on butadiene comonomer, isoprene comonomer, styrene-butadiene comonomer, and alkyl acrylate, b) from 70 to 97% by weight, particularly preferably from 85 to 95% by weight, based on styrene and/or polyalkyl ester c) from 0 to 5% by weight based on unsaturated nitrile monomers d) from 0 to 40% by weight based on acrylic acid, methacrylic acid, maleic anhydride, or N-substituted maleimide.

It is preferable that the thermoplastic polymers are halogen-containing polymers, e.g. polychloroprene, chlorinated rubber, chlorinated and brominated copolymer composed of isobutylene-isoprene (halobutyl rubber), chlorinated or chlorosulfonated polyethylene, copolymers of ethylene and of chlorinated ethylene, epichlorohydrin homo- and copolymers, in particular polymers composed of halogen-containing vinyl compounds, e.g. polyvinyl chloride, polyvinylidene chloride, polyvinyl fluoride, polyvinylidene fluoride; or else copolymers of these, such as vinyl chloride-vinylidene chloride, vinyl chloride-vinyl acetate, or vinylidene chloride-vinyl acetate.

It is preferable that the thermoplastic polymers are polymers which derive from alpha-beta-unsaturated acids and from their derivatives, e.g. polyacrylates and polymethacrylates, butyl-acrylate-impact-modified polymethyl methacrylates, polyacrylamides and polyacrylonitriles, and copolymers of the monomers mentioned with one another or with other unsaturated monomers, e.g. acrylonitrile-butadiene copolymers, acrylonitrile-alkyl acrylate copolymers, acrylonitrile-alkoxyalkyl acrylate copolymers, acrylonitrile-vinyl halide copolymers, or acrylonitrile-alkyl methacrylate-butadiene terpolymers.

It is preferable that the thermoplastic polymers are polymers which derive from unsaturated alcohols and amines or from their acyl derivatives or acetals, e.g. polyvinyl alcohol, polyvinyl acetate, polyvinyl stearate, polyvinyl benzoate, polyvinyl maleate, polyvinyl butyral, polyallyl phthalate, polyallylmelamine; or else their copolymers with olefins.

It is preferable that the thermoplastic polymers are homo- and copolymers of cyclic ethers, e.g. polyalkylene glycols, polyethylene oxide, polypropylene oxide, or their copolymers with bisglycidyl ethers.

It is preferable that the polymers are thermoplastic polyacetals, such as polyoxymethylene, or else those polyoxymethylenes which contain comonomers, e.g. ethylene oxide; polyacetals modified with thermoplastic polyurethanes, or with acrylates, or with MBS.

It is preferable that the thermoplastic polymers are polyphenylene oxides and polyphenylene sulfides, and their mixtures with styrene polymers or with polyamides.

The thermoplastic polymers are preferably polyphenylene ethers, such as poly(2,6-dimethyl-1,4-phenylene) ether, poly(2,6-diethyl-1,4-phenylene) ether, poly(2,6-dipropyl-1,4-phenylene) ether, poly(2-methyl-6-ethyl-1,4-phenylene) ether, poly(2-methyl-6-propyl-1,4-phenylene) ether, poly(2-ethyl-6-propyl-1,4-phenylene) ether, poly(2,6-diphenyl-1,4-phenylene) ether, copolymer of poly(2,6-dimethyl-1,4-phenylene) ether and poly(2,3,6-trimethyl-1,4-phenylene) ether, copolymer of poly(2,6-dimethyl-1,4-phenylene) ether and poly(2,3,6-triethyl-1,4-phenylene) ether.

It is preferable that the polyphenylene ethers are poly(2,6-dimethyl-1,4-phenylene) ether from Asahi Kasei Co. of Japan (grade S-202).

It is preferable that the thermoplastic polymers are polyurethanes which derive firstly from polyethers, from polyesters, and from polybutadienes having terminal hydroxy groups, and secondly from aliphatic or aromatic polyisocyanates, or else their precursors.

It is preferable that the thermoplastic polymers are polyamides and copolyamides derived from diamines and dicarboxylic acids, and/or from aminocarboxylic acids, or from the corresponding lactams, for example nylon-4, nylon-6 (®Akulon K122, DSM; ®Zytel 7301, DuPont; ®Durethan B 29, Bayer), nylon-6,6 (®Zytel 101, DuPont; ®Durethan A30, ®Durethan AKV, ®Durethan AM, Bayer; ®Ultramid A3, BASF)-6,10, -6,9, -6,12, -4,6, -12,12, nylon-11, and nylon-12 (®Grillamid L20, Ems Chemie), aromatic polyamides based on m-xylene, diamine and adipic acid; polyamides prepared from hexamethylenediamine and iso- and/or terephthalic acid and, where appropriate, an elastomer as modifier, e.g. poly-2,4,4-trimethylhexamethyleneterephthalamide or poly-m-phenyleneisophthalamide. Other suitable polymers are block copolymers of the abovementioned polyamides with polyolefins, with olefin copolymers, with ionomers, or with chemically bonded or grafted elastomers; or with polyethers, e.g. with polyethylene glycol, polypropylene glycol, or polytetramethylene glycol. EPDM- or ABS-modified polyamides or copolyamides are also suitable, as are polyamides condensed during processing ("RIM polyamide systems").

It is preferable that the polymers are polyureas, polyimides, polyamideimides, polyetherimides, polyesterimides, polyhydantoins and polybenzimidazoles.

It is preferable that the thermoplastic polymers are polyesters which derive from dicarboxylic acids and dialcohols and/or from hydroxycarboxylic acids, or from the corresponding lactones, for example polyethylene terephthalate, polybutylene terephthalate (®Celanex 2500, ®Celanex 2002, Celanese; ®Ultradur, BASF), poly-1,4-dimethylolcyclohexane terephthalate, polyhydroxybenzoates, and also block polyetheresters which derive from polyethers having hydroxyl end groups; as well as polyesters modified with polycarbonates or with MBS.

It is preferable that the thermoplastic polymers are polycarbonates or polyester carbonates, or else polysulfones, polyether sulfones, or polyether ketones.

It is preferable that the polymers are mixtures (polyblends) of the abovementioned polymers, e.g. PP/EPDM, nylon/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PU, PC/thermoplastic PU, POM/acrylate, POM/MBS, PPO/HIPS, PPO/nylon-6,6 and copolymers, PA/HDPE, PA/PP, PA/PPO, PBT/PC/ABS, and PBT/PET/PC.

It is preferable that the inventive salts of alkyl esters of carboxyethyl(alkyl)phosphinic acid are used for production of flame-retardant polymer moldings, of flame-retardant polymer films, of flame-retardant polymer filaments, or of flame-retardant polymer fibers.

It is preferable that the flame-retardant polymer moldings, flame-retardant polymer films, flame-retardant polymer filaments, and flame-retardant polymer fibers comprise from 0.5 to 45% by weight of inventive salts of alkyl esters of carboxyethyl(alkyl)phosphinic acid and from 0.5 to 95% by weight of thermoplastic polymer, or a mixture of these.

It is preferable that the flame-retardant polymer moldings, flame-retardant polymer films, flame-retardant polymer filaments, and flame-retardant polymer fibers comprise from 0.5 to 45% by weight of inventive salts of alkyl esters of carboxyethyl(alkyl)phosphinic acid, and from 0.5 to 95% by weight of thermoplastic polymer or a mixture of these, from 0.5 to 55% by weight of additives, and from 0.5 to 55% by weight of filler or reinforcing materials.

It is preferable that the flame-retardant polymer moldings, flame-retardant polymer films, flame-retardant polymer filaments, and flame-retardant polymer fibers comprise from 0.1 to 35% by weight of salts of alkyl esters of carboxyethyl(alkyl)phosphinic acid of type (I) or (II), from 15 to 80% by weight of polystyrene-based polymer, and from 15 to 80% by weight of polyphenylene ether, from 0.5 to 55% by weight of additives, and from 0 to 55% by weight of filler or reinforcing materials.

It is preferable that the inventive flame-retardant thermoplastic polymer molding compositions are used for the production of flame-retardant polymer moldings, of flame-retardant polymer films, of flame-retardant polymer filaments, and of flame-retardant polymer fibers.

It is preferable that the flame-retardant polymer moldings, flame-retardant polymer films, flame-retardant polymer filaments, and flame-retardant polymer fibers comprise from 40 to 99.5% by weight of inventive flame-retardant thermoplastic polymer molding compositions and from 0.5 to 60% by weight of thermoplastic polymer or a mixture of these.

Finally, the invention also provides a process for production of flame-retardant polymer moldings, which comprises using injection molding (e.g. an injection-molding machine (Arburg Allrounder)) and compression molding, foam injection molding, internal-gas-pressure injection molding, blow-molding, cast-film production, calendering, lamination, or coating, at relatively high temperatures, to process inventive flame-retardant polymer molding compositions to give the flame-retardant polymer molding.

It is preferable that the inventive salts of alkyl esters of carboxyethyl(alkyl)phosphinic acid are used for the preparation of flame-retardant thermoset polymer molding compositions.

Finally, the invention also provides a flame-retardant thermoset polymer molding composition comprising from 0.1 to 45% by weight of inventive salts of alkyl esters of carboxyethyl(alkyl)phosphinic acid, of type (I) or (II), from 40 to 90% by weight of unsaturated polyester, and from 10 to 60% by weight of vinyl monomer.

It is preferable that the thermoset polymers are unsaturated polyester resins which derive from copolyesters of saturated or unsaturated dicarboxylic acids or from their anhydrides with polyhydric alcohols, and also vinyl compounds as crosslinking agents. UP resins are hardened via free-radical polymerization, using initiators (e.g. peroxides) and accelerators.

Preferred unsaturated dicarboxylic acids and unsaturated dicarboxylic acid derivatives for the preparation of the polyesters are maleic anhydride and fumaric acid.

Preferred saturated dicarboxylic acids are phthalic acid, isophthalic acid, terephthalic acid, tetrahydrophthalic acid, and/or adipic acid.

Preferred diols are 1,2-propanediol, ethylene glycol, diethylene glycol, and neopentyl glycol, neopentyl glycol, and ethoxylated or propoxylated bisphenol A.

Preferred vinyl compound for the crosslinking reaction is styrene.

Preferred hardener systems are peroxides and metal coinitiators, e.g. hydroperoxides, and cobalt octanoate, and/or benzoyl peroxide, and aromatic amines, and/or UV light and photosensitizers, e.g. benzoin ethers.

Preferred hydroperoxides are di-tert-butyl peroxide, tert-butyl peroctoate, tert-butyl perpivalate, tert-butyl 2-ethylperhexanoate, tert-butyl permaleate, tert-butyl periso-butyrate, benzoyl peroxide, diacetyl peroxide, succinyl peroxide, p-chlorobenzoyl peroxide, dicyclohexyl peroxydicarbonate.

It is preferable that the amounts used of initiators are from 0.1 to 20% by weight, with preference from 0.2 to 15% by weight, based on the weight of all the comonomers.

Preferred metal coinitiators are compounds of cobalt, of manganese, of iron, of vanadium, of nickel, or of lead. It is preferable to use amounts of from 0.05 to 1% by weight, based on the weight of all of the comonomers, of metal coinitiators.

Preferred aromatic amines are dimethylaniline, p-dimethyltoluene, diethylaniline and phenyldiethanolamines.

A process for the preparation of flame-retardant copolymers comprises copolymerizing (A) at least one ethylenically unsaturated dicarboxylic anhydride, derived from at least one $C_4$-$C_8$ dicarboxylic acid, (B) at least one vinylaromatic compound and (C) a polyol, and then (D) reacting with inventive salts of alkyl esters of carboxyethyl(alkyl)phosphinic acid.

A process for preparation of flame-retardant thermoset compositions comprises mixing a thermoset resin with inventive salts of alkyl esters of carboxyethyl(alkyl)phosphinic acid, the resultant mixture being wet-pressed (cold pressing) at pressures of from 3 to 10 bar and temperatures of from 20 to 60° C.

Another process for preparation of flame-retardant thermoset compositions comprises mixing a thermoset resin with inventive salts of alkyl esters of carboxyethyl(alkyl)phosphinic acid, the resultant mixture being wet-pressed (warm or hot pressing) at pressures of from 3 to 10 bar and temperatures of from 80 to 150° C.

The invention therefore also provides a flame-retardant epoxy resin, comprising from 0.5 to 50% by weight of the inventive salts of alkyl esters of carboxyethyl(alkyl)phosphinic acid, of type (I) or (II), from 5 to 70% by weight of an epoxy resin, and from 0 to 20% by weight of a hardener.

It is preferable that these are crosslinked epoxy resins which derive from aliphatic, cycloaliphatic, heterocyclic, or aromatic glycidyl compounds, e.g. products of bisphenol A diglycidyl ethers, or of bisphenol F diglycidyl ethers, which are crosslinked by means of conventional hardeners and/or accelerators.

Suitable glycidyl compounds are bisphenol A diglycidyl ester, bisphenol F diglycidyl ester, polyglycidyl ester of phenol-formaldehyde resins and of cresol-formaldehyde resins, polyglycidyl ester of phthalic, isophthalic, and terephthalic acid, and also of trimellitic acid, N-glycidyl compounds of aromatic amines and of heterocyclic nitrogen bases, and also di- and polyglycidyl compounds of polyhydric aliphatic alcohols.

Suitable hardeners are polyamines, such as diethylenetriamine, triethylenetetramine, aminoethylpiperazine, isophoronediamine, polyamidoamine, diaminodiphenylmethane, diaminodiphenol sulfones, and dicyandiamide.

Suitable hardeners are polybasic acids or their anhydrides, e.g. phthalic anhydride, maleic anhydride, tetrahydrophthalic anhydride, methyltetrahydrophthalic anhydride, hexahydrophthalic anhydride, and methylhexahydrophthalic anhydride.

Suitable hardeners are phenols, e.g. phenol-novolak resin, cresol-novolak resin, dicyclopentadiene-phenol-adduct resin, phenol-aralkyl-resin, cresol-aralkyl resin, naphthol-aralkyl resin, biphenol-modified phenol-aralkyl resin, phenol-trimethylolmethane resin, tetraphenylolethane resin, naphthol-novolak resin, naphthol-phenol cocondensate resin, naphthol-cresol cocondensate resin, biphenol-modified phenolic resin, and aminotriazine-modified phenolic resin.

These hardeners can be used alone or in combination with one another.

Suitable catalysts or accelerators for the crosslinking process during the polymerization process are tertiary amines, benzyldimethylamine, N-alkylpyridines, imidazole, 1-methylimidazole, 2-methylimidazole, 2-ethyl-4-methylimidazole, 2-ethyl-4-methylimidazole, 2-phenylimidazole, 2-heptadecylimidazole, metal salts of organic acids, Lewis acids, and amine complex salts.

Epoxy resins rendered flame-retardant by the invention are suitable for the potting of electrical or electronic components and for saturation and impregnation processes. In electrical engineering, the epoxy resins used have mainly been rendered flame-retardant and are used for printed circuit boards and for insulators.

It is preferable that the polymers are crosslinked polymers which derive on the one hand from aldehydes and on the other hand from phenols, urea, or melamine, examples being phenol-formaldehyde resins, urea-formaldehyde resins, and melamine-formaldehyde resins.

It is preferable that the polymers are crosslinkable acrylic resins which derive from substituted acrylates, e.g. from epoxy acrylates, from urethane acrylates, or from polyester acrylates.

It is preferable that the polymers are alkyd resins, polyester resins, and acrylate resins, crosslinked with melamine resins, with urea resins, with isocyanates, with isocyanurates, with polyisocyanates, or with epoxy resins.

It is preferable that the inventive flame-retardant epoxy resins are used for the production of flame-retardant thermoset polymer moldings.

The invention also provides a flame-retardant polyurethane molding composition, prepared via reaction of from 0.1 to 50 parts by weight of inventive salt of alkyl esters of carboxyethyl(alkyl)phosphinic acid, from 30 to 65 parts by weight of polyisocyanate, and from 30 to 65 parts by weight of polyol.

The invention also provides a process for preparation of a flame-retardant polyurethane molding composition, by reacting from 170 to 70 parts by weight, preferably from 130 to 80 parts by weight, of polyisocyanates with 100 parts by weight of polyol, from 0.1 to 50 parts by weight of inventive salt of alkyl esters of carboxyethyl(alkyl)phosphinic acid, and from 0.1 to 4 parts by weight, preferably from 1 to 2 parts by weight, of catalyst, and optionally foaming with from 0.1 to 1.8 parts by weight, preferably from 0.3 to 1.6 parts by weight, of blowing agent.

It is preferable that the flame-retardant polyurethane molding compositions are used for the production of flame-retardant thermoset polymer moldings.

Preferred polyols are alkene oxide adducts of ethylene glycol, 1,2-propanediol, bisphenol A, trimethylolpropane, glycerol, pentaerythrol, sorbitol, sugars, degraded starch, ethylenediamine, diaminotoluene, and/or aniline, these serving as an initiator. The preferred alkoxylating agents contain from 2 to 4 carbon atoms, particular preference being given to ethylene oxide and propylene oxide.

Preferred polyester polyols are obtained via polycondensation of a polyalcohol, such as ethylene glycol, diethylene glycol, propylene glycol, 1,4-butanediol, 1,5-pentanediol, methylpentanediol, 1,6-hexanediol, trimethylolpropane, glycerol, pentaerythritol, diglycerol, glucose and/or sorbitol, with a dibasic acid, such as oxalic acid, malonic acid, succinic acid, tartaric acid, adipic acid, sebacic acid, maleic acid, fumaric acid, phthalic acid, terephthalic acid. These polyester polyols can be used alone or in combination.

Preferred polyisocyanates are aromatic, alicyclic, or aliphatic polyisocyanates having two or more isocyanate groups, and mixtures of these. Preference is given to aromatic polyisocyanates, such as tolyl diisocyanate, methylenediphenyl diisocyanate, naphthylene diisocyanates, xylylene diisocyanate, tris(4-isocyanatophenyl)methane, and polymethylene polyphenylene diisocyanates; alicyclic polyisocyanates are methylenediphenyl diisocyanate and tolyl diisocyanate; aliphatic polyisocyanates are hexamethylene diisocyanate, isophorene diisocyanate, demeryl diisocyanate, 1,1-methylenebis(4-isocyanatocyclohexane-4,4'-diisocyanatodicyclohexylmethane isomer mixture, cyclohexyl 1,4-diisocyanate, ®Desmodur grades (Bayer), and lysine diisocyanate, and mixtures of these.

Modified products obtained via reaction of polyisocyanate with polyol, urea, carbodiimide, and/or biuret are suitable polyisocyanates.

Suitable catalysts are strong bases, alkali metal salts of carboxylic acids, or aliphatic tertiary amines. Preference is given to quaternary ammonium hydroxides, alkali metal hydroxide or alkoxide, sodium or potassium acetate, potassium octoate, sodium benzoate, 1,4-diazabicyclo[2.2.2]octane, N,N,N',N'-tetramethylhexamethylenediamine, N,N,N',N'-tetramethylpropylenediamine, N,N,N',N',N''-pentamethyl-diethylenetriamine, N,N'-di-($C_1$-$C_2$)-alkylpiperazine, trimethylaminoethylpiperazine, N,N-dimethylcyclohexylamine, N,N-dimethylbenzylamine, N-methylmorpholine, N-ethylmorpholine, trimethylamine, triethylamine, tributylamine, triethylenediamine, bis(dimethylaminoalkyl)piperazine, N,N,N',N'-tetramethylethylenediamine, N,N-diethylbenzylamine, bis(N,N-diethylaminoethyl) adipate, N,N,N',N'-tetramethyl-1,3-butanediamine, N,N-diethyl[beta]phenylethylamine, 1,2-dimethylimidazole, 2-methylimidazole etc.

It is preferable that the ratio by weight of the polyisocyanates to polyol is from 170 to 70, preferably from 130 to 80, based on 100 parts by weight of the polyol.

It is preferable that the ratio by weight of the catalyst is from 0.1 to 4 parts by weight, particularly preferably from 1 to 2 parts by weight, based on 100 parts by weight of the polyol.

Preferred blowing agents are water, hydrocarbons, fluorochlorocarbons, fluorocarbons, etc.

The amount of the blowing agent is from 0.1 to 1.8 parts by weight, preferably from 0.3 to 1.6 parts by weight, and in particular from 0.8 to 1.6 parts by weight, based on 100 parts by weight of the polyol.

The invention also provides an intumescent flame-retardant coating comprising from 1 to 50% of inventive salts of alkyl esters of carboxyethyl(alkyl)phosphinic acid, from 0 to 60% of ammonium polyphosphate, and also from 0 to 80% by weight of binders, foam-formers, fillers, and additives.

The invention also provides an intumescent flame-retardant coating comprising from 1 to 99% by weight of an epoxy resin and from 1 to 99% by weight of a flame retardant mixture which comprises a phosphorus-nitrogen flame retardant and inventive salts of alkyl esters of carboxyethyl(alkyl)phosphinic acid, and from 0 to 60% by weight of other additives.

It is preferable that the phosphorus-nitrogen flame retardants are ammonium polyphosphates of the formula $(NH_4PO_3)_n$, in which n is a number from 10 to greater than or equal to 1000, preferably from 200 to greater than or equal to 1000.

Preparation/production, processing, and testing of flame-retardant plastics molding compositions and of plastics moldings The flame retardant components were mixed with the polymer pellets and optionally with additives, and incorporated in a twin-screw extruder. The homogenized polymer strand was drawn off, cooled in a water bath, and then pelletized.

After adequate drying, the molding compositions were processed in an injection-molding machine (Arburg Allrounder) to give test specimens.

The UL 94 (Underwriters Laboratories) fire classification was determined on test specimens composed of each mixture, using test specimens of thickness 1.5 mm.

The UL 94 fire classification system is as follows:

V-0: afterflame time never longer than 10 sec, total of afterflame times for 10 flame applications not more than 50 sec, no flaming drops, no complete consumption of the specimen, afterglow time for specimens never longer than 30 sec after end of flame application.

V-1: afterflame time never longer than 30 sec after end of flame application, total of afterflame times for 10 flame applications not more than 250 sec, afterglow time for specimens never longer than 60 sec after end of flame application, other criteria as for V-0

V-2: cotton indicator ignited by flaming drops; other criteria as for V-1 ncl: not classifiable, does not comply with fire classification V-2.

Preparation of Flame-Retardant Thermoset Epoxy Molding Compositions and Production of Flame-Retardant Thermoset Epoxy Moldings The epoxy resin and the flame retardant components were homogeneously mixed, using a dissolver disk. After addition of the hardener, the mixture was again homogenized. Two layers of continuous glass textile mat whose weight per unit area was 450 g/m$^2$ were inserted within a heated press, on a Hostaphan® release film and a steel frame. About half of the resin/flame retardant mixture was then uniformly distributed. Another glass mat was added, and then the remaining resin/flame retardant mixture distributed, the laminate was covered with a release film, and pressed plaque of thickness 1.5 mm was produced at a temperature of 50° C. over a period of one hour, using a pressure of 10 bar. UL 94 (Underwriters Laboratories) fire classification was determined on test specimens of length 127 mm and width 12.7 mm, using test specimens of thickness 1.5 mm.

General Specification for Determination of Exudation 50 g of flame-retardant polymer molding composition pellets or laminate comminuted to pellet size are stored for 500 h at 60° C. at 95% rel. humidity. The pellets are then immersed for 2 h in a 0.1% strength aqueous sodium hydroxide solution at room temperature. P content of the solution isolated is studied. The leached phosphorus is expressed as a percentage based on the amount used in the molding composition.

The invention is illustrated in more detail by the examples below.

EXAMPLES 1 to 3

The amounts described in Table 1 of Exolit® PE110 and MeOH were weighed into a nitrogen-inertized four-liter five-necked flask with superposed reflux condenser, stirrer with precision glass gland, and thermometer, and stirred at from 40-80° C. for about 48-62 h. The solvent loss by evaporation is replaced after cooling.

EXAMPLE 4

The amounts described in Table 1 of Exolit® PE110 and n-octanol were weighed into a nitrogen-inertized two-liter five-necked flask with superposed reflux condenser, stirrer with precision glass gland, and thermometer, and stirred at 60° C. for about 60 h.

EXAMPLE 5

The amounts described in Table 1 of Exolit® PE110 and benzyl alcohol were weighed into a nitrogen-inertized two-liter five-necked flask with superposed reflux condenser, stirrer with precision glass gland, and thermometer, and stirred at 60° C. for about 70 h.

EXAMPLES 6 TO 9

Methyl ester solutions were neutralized with cooling to at most 60° C. using the amounts described in Table 1 of 25% by weight sodium hydroxide solution, 50% by weight sodium hydroxide solution, aqueous NaHCO$_3$ solution, and aqueous K$_2$CO$_3$ solution.

EXAMPLE 10

Demineralized water is used as initial charge in a two-liter five-necked round-bottomed flask with stirrer with precision glass gland, thermometer, reflux condenser, and two pump inlets. An aqueous solution of the sodium salt of the methyl ester of carboxyethyl(methyl)phosphinic acid is pumped into the flask within a period of 2 h by way of pump 1, and Al sulfate solution (to which sulfuric acid has been admixed) is simultaneously pumped into the flask by way of pump 2, using a stirrer speed of from 400 to 550 rpm (see Table 1 for conditions), at a reaction temperature of 90° C. After a continued-stirring time of 30 minutes, the wet solids were filtered off by way of a suction funnel (240 mm), the filter cake was redispersed with five times the amount of water at 70° C. for 2 h, and the resulting wet solid was again filtered and washed with water at 90° C. (5 times the amount). The product, moist from the filter, was dried in a vacuum drying cabinet at from 30 to 100 mbar, at 130° C., for 15 h. X-ray analysis shows that the product is crystalline. The following reflections are observed: rel. intensity in %, d value in Ang; 100.00, 11.6890; 56.48, 7.3783; 62.07, 4.4543; 80.31, 4.2741. (CuKalpha1 radiation 1.54056 Ang).

The product decomposes in differential thermal analysis at 330° C. and is more reactive than a flame retardant of the prior art.

EXAMPLE 11

The amounts mentioned in Table 1 of methyl ester of carboxyethyl(methyl)phosphinic acid and of demineralized water were used as initial charge in a two-liter five-necked round-bottomed flask, and magnesium hydroxide was admixed. The pH rises to from 4.82 to 5.15 with a slight rise in temperature to 30° C. The wet solids were boiled at reflux for 5 h, cooled, and filtered to give a clear solution by way of a suction funnel, and a rotary evaporator was used to concentrate the filtrate to about 40-50% solid. Acetone was admixed with the residue. The precipitate was filtered in a suction funnel, washed with acetone, and dried in a vacuum drying cabinet at 120° C. and 100 mbar for 18 h. X-ray analysis shows that the product is crystalline. The following reflections are observed: rel. intensity in %, d value in Ang; 36.02, 8.9271; 25.94, 8.3244; 64.37, 4.7600; 100.00, 4.4639; 99.14, 4.2948; 71.27, 3.7785; 54.91, 3.5518. (CuKalpha1 radiation 1.54056 Ang).

The product decomposes in differential thermal analysis at 282° C. and is more reactive than a flame retardant of the prior art.

EXAMPLE 12

The amounts mentioned in Table 1 of methyl ester of carboxyethyl(methyl)phosphinic acid and of demineralized water were used, as initial charge in a two-liter five-necked round-bottomed flask, and zinc oxide was admixed. The wet solids were boiled at reflux for 5 h, cooled, and filtered to give a clear solution by way of a suction funnel, and a rotary evaporator was used to concentrate the filtrate to about 30-40% solid. The solution was cooled to about 5° C. using ice/water, and the precipitate was filtered off in a suction funnel. The filter cake was washed with acetone, and dried in a vacuum drying cabinet at 120° C. and 100 mbar for 18 h.

X-ray analysis shows that the product is crystalline. The following reflections are observed: rel. intensity in %, d value in Ang; 100.00, 8.5927; 70.47, 5.5696; 68.34, 4.2808. (CuKalpha1 radiation 1.54056 Ang).

The product decomposes in differential thermal analysis at 334° C. and is more reactive than a flame retardant of the prior art.

EXAMPLE 13

The amounts mentioned in Table 1 of methyl ester of carboxyethyl(methyl)phosphinic acid and of demineralized water were used as initial charge in a two-liter five-necked round-bottomed flask, and calcium hydroxide was admixed. The pH rises to 5.4 with a slight rise in temperature to 50° C.

The wet solids were boiled at reflux for 5 h, cooled, and filtered to give a clear solution by way of a suction funnel, and a rotary evaporator was used to concentrate the filtrate to about 37-42% solid. Acetone was admixed with the concentrated solution, and the precipitate was filtered off in a suction funnel. The filter cake was washed with acetone and dried in a vacuum drying cabinet at 120° C. and 100 mbar for 18 h. X-ray analysis shows that the product is crystalline. The following reflections are observed: rel. intensity in %, d value in Ang; 75.31, 10.9469; 100.00, 5.4514; 60.15, 4.3041; 66.50, 2.1819. (CuKalpha1 radiation 1.54056 Ang).

The product decomposes in differential thermal analysis at 317° C. and is more reactive than a flame retardant of the prior art.

EXAMPLE 14

The amounts mentioned in Table 1 of methyl ester of carboxyethyl(methyl)phosphinic acid were used as initial charge in a two-liter five-necked round-bottomed flask, and zinc oxide was admixed. The wet solids were boiled at reflux for 5 h and cooled, and the precipitate was filtered off in a suction funnel. The filter cake was repeatedly washed with acetone, and dried in a vacuum drying cabinet at 120° C. and 100 mbar for 18 h.

The product decomposes in differential thermal analysis at 323° C. and is more reactive than a flame retardant of the prior art.

EXAMPLE 15

The amounts mentioned in Table 1 of the methyl ester of carboxyethyl(methyl)phosphinic acid were used as initial charge in a two-liter five-necked round-bottomed flask, and magnesium hydroxide was admixed. The wet solids were boiled at reflux for 5 h and cooled, and the precipitate was filtered off in a suction funnel. The filter cake was repeatedly washed with acetone and dried in a vacuum drying cabinet at 120° C. and 100 mbar for 18 h. The product decomposes in differential thermal analysis at 275° C. and is more reactive than a flame retardant of the prior art.

EXAMPLE 16

The decomposition temperature and the average particle diameter are determined on a flame retardant of the prior art—Exolit® OP 1230. Table 1 lists the data.

EXAMPLE 17

Comparison

A mixture of 30% by weight of product from EP-A-1 125 960, 1-methylimidazolium (2-methoxycarbonylethyl)(methyl)phosphinate and 70% by weight of polystyrene is compounded in accordance with the general specification for "Preparation/production, processing, and testing of flame-retardant plastics molding compositions and of plastics moldings", in a twin-screw extruder at 170° C., with considerable smoke generation, to give a flame-retardant polymer molding composition. The smoke is attributable to decomposition of the flame retardant, and is evaluated as an adverse factor. The homogenized polymer strand is drawn off, cooled in a water bath, and then pelletized. The molding compositions are dried and then processed at melt temperatures of from 200 to 250° C. in an injection-molding machine, to give polymer moldings. The test specimen achieves UL 94 V-2 classification. Testing to the appropriate general specification reveals that 24% of the flame retardant exudes.

EXAMPLE 18

In accordance with the general specification for "Preparation/production, processing, and testing of flame-retardant plastics molding compositions and of plastics moldings", a mixture of 30% by weight of product from example 10 and 70% by weight of polystyrene is compounded in a twin-screw extruder at 170° C. to give a flame-retardant polymer molding composition. The homogenized polymer strand is drawn off, cooled in a water bath, and then pelletized. The molding compositions are dried and then processed at melt temperatures of from 200 to 250° C. in an injection-molding machine to give flame-retardant polymer moldings. The test specimen achieves UL 94 V-0 classification.

Testing to the appropriate general specification reveals that 4% of the flame retardant exudes. This is very much less than in comparative example 17 using a flame retardant of the prior art.

EXAMPLE 19

In accordance with the general specification for "Preparation/production, processing, and testing of flame-retardant plastics molding compositions and of plastics moldings", a mixture of 23% by weight of product from example 10 and 47% by weight of polystyrene, and 30% by weight of glass fibers is compounded in a twin-screw extruder at 170° C. to give a flame-retardant polymer molding composition. The homogenized polymer strand is drawn off, cooled in a water bath, and then pelletized. The molding compositions are dried and then processed at melt temperatures of from 200 to 250° C. in an injection-molding machine to give flame-retardant polymer moldings. The test specimen achieves UL 94 V-0 classification.

Testing to the appropriate general specification reveals that 4% of the flame retardant exudes. This is very much less than in comparative example 17 using a flame retardant of the prior art.

EXAMPLE 20

In accordance with the general specification for "Preparation/production, processing, and testing of flame-retardant plastics molding compositions and of plastics moldings", a mixture of 12% by weight of product from example 10, 6% by weight of melamine cyanurate, 52% by weight of polybutylene terephthalate, and 30% by weight of glass fibers is compounded in a twin-screw extruder at from 230 to 260° C. to give a flame-retardant polymer molding composition. The homogenized polymer strand is drawn off, cooled in a water bath, and then pelletized. The molding compositions are dried and then processed at melt temperatures of from 240 to 270° C. in an injection-molding machine to give flame-retardant polymer moldings. The test specimen achieves UL 94 V-0 classification.

Testing to the appropriate general specification reveals that 4% of the flame retardant exudes. This is very much less than in comparative example 17 using a flame retardant of the prior art.

EXAMPLE 21

In accordance with the general specification for "Preparation/production, processing, and testing of flame-retardant plastics molding compositions and of plastics moldings", a mixture of 11.4% by weight of product from example 1, 5.7% by weight of melamine polyphosphate, 0.9% by weight of zinc borate, 52% by weight of nylon-6,6, and 30% by weight of glass fibers is compounded in a twin-screw extruder at from 260 to 280° C. to give a flame-retardant polymer molding composition. The homogenized polymer strand is drawn off, cooled in a water bath, and then pelletized. The molding compositions are dried and then processed at melt temperatures of from 260 to 290° C. in an injection-molding machine to give flame-retardant polymer moldings. The test specimen achieves UL 94 V-0 classification.

Testing to the appropriate general specification reveals that 8% of the flame retardant exudes. This is very much less than in comparative example 17 using a flame retardant of the prior art.

EXAMPLE 22

In accordance with the general specification for "Preparation/production, processing, and testing of flame-retardant plastics molding compositions and of plastics moldings", a mixture of 20% by weight of product from example 12, 50% by weight of nylon-6, and 30% by weight of glass fibers is compounded in a twin-screw extruder at from 260 to 280° C. to give a flame-retardant polymer molding composition. The homogenized polymer strand is drawn off, cooled in a water bath, and then pelletized. The molding compositions are dried and then processed at melt temperatures of from 260 to 290° C. in an injection-molding machine to give flame-retardant polymer moldings. The test specimen achieves UL 94 V-0 classification.

Testing to the appropriate general specification reveals that 6% of the flame retardant exudes. This is very much less than in comparative example 17 using a flame retardant of the prior art.

EXAMPLE 23

Comparison

In accordance with the general specification for "Preparation of flame-retardant thermoset epoxy molding compositions and production of flame-retardant thermoset epoxy moldings", a flame-retardant epoxy resin laminate is produced using 17% by weight of flame retardant from EP-A-1 125 960, 1-methylimidazolium (2-methoxycarbonylethyl)(methyl)phosphinate and the amounts listed in Table 2 of resin and of hardener. The test specimen achieves UL 94 V-1 classification.

Testing to the appropriate general specification reveals that 15% of the flame retardant exudes.

EXAMPLE 24

In accordance with the general specification for "Preparation of flame-retardant thermoset epoxy molding compositions and production of flame-retardant thermoset epoxy moldings", a flame-retardant epoxy resin laminate is produced using 17% by weight of flame retardant from example 11 and the amounts listed in Table 2 of resin and of hardener.

The test specimen achieves UL 94 V-0 classification.

Testing to the appropriate general specification reveals that 6% of the flame retardant exudes. This is very much less than in comparative example 22 using a flame retardant of the prior art.

TABLE 3

| | Other chemicals used |
|---|---|
| PS1 | Polystyrene 2712, BASF |
| PS2 | Polystyrene 143 E, BASF |
| PBT | Celanex ® 2500, Celanese, USA |
| GF 1 | Vetrotex ® EC 10 983, 4.5 mm, Saint Gobain |
| PA66 | Ultramid ® A3, BASF |
| MC | Melapur ® MC, Ciba SC |
| ZB | Firebrake ® 500, Borax |
| PA6 | Zytel ® 7301, DuPont |
| MPP | Melapur ® 200/70, Ciba SC |
| EP | Beckopox ® EP 140 epoxy resin, Cytec |
| EH | Beckopox ® EH 625 hardener, Cytec |

TABLE 1

Inventive alkyl esters of carboxyethyl(methyl)phosphinic acid and their salts

| | Component | | | | | | | | Product | | | | |
|---|---|---|---|---|---|---|---|---|---|---|---|---|---|
| | 1 | | 2 | | 3 | 4 | T | t | pH | Yield | Content | 31P | DTA | d50 |
| Example | Name | [g] | Name | [g] | [g] | [g] | [° C.] | [h] | — | [%] | [P-%] | [ppm] | [° C.] | [m] |
| 1 | Oxa | 143 | MeOH | 214 | — | — | 40 | 48 | 2.4 | 51 | 51 | 51.6 | — | — |
| 2 | Oxa | 1242 | MeOH | 1900 | — | — | 60 | 54 | 1.7 | 55 | 55 | 51.6 | — | — |
| 3 | Oxa | 1152 | MeOH | 1762 | — | — | 80 | 62 | 1.4 | 56 | 56 | 51.6 | — | — |
| 4 | Oxa | 446 | OctOH | 433 | — | — | 60 | 60 | 1.9 | 52 | 52 | 47.8 | — | — |
| 5 | Oxa | 473 | BzOH | 382 | — | — | 60 | 70 | 1.5 | 49 | 49 | — | — | — |
| 6 | Ex. 2 | 985 | NaOH 25% | 272 | — | — | 40 | — | 6.2 | 87 | 48 | 38.6 | — | — |
| 7 | Ex. 2 | 1005 | NaOH 50% | 139 | — | — | 20 | — | 8.5 | 90 | 50 | 38.6 | — | — |
| 8 | Ex. 2 | 1084 | NaHCO3 soln | 293 | — | — | 40 | — | 6.2 | 92 | 51 | 38.6 | — | — |
| 9 | Ex. 2 | 1037 | K2CO3 soln | 215 | — | — | 60 | — | 6.4 | 88 | 49 | 38.6 | — | — |

TABLE 1-continued

Inventive alkyl esters of carboxyethyl(methyl)phosphinic acid and their salts

| | Component | | | | | | | | Product | | | | |
|---|---|---|---|---|---|---|---|---|---|---|---|---|---|
| | 1 | | 2 | | 3 | 4 | T | t | pH | Yield | Content | 31P | DTA | d50 |
| Example | Name | [g] | Name | [g] | [g] | [g] | [°C.] | [h] | — | [%] | [P-%] | [ppm] | [°C.] | [m] |
| 10 | Ex. 8 | 1200 | Water | 1111 | 370 | 4.4 | 90 | 2 | — | 76 | 17.7 | about 58.3 | 330 | 52 |
| 11 | Ex. 2 | 1067 | Water | 227 | 50.4 | — | 100 | 5 | 5.2 | 87 | 17.5 | — | 282 | 26 |
| 12 | Ex. 2 | 1067 | Water | 252 | 70.4 | — | 100 | 5 | — | 88 | 15.7 | — | 334 | 19 |
| 13 | Ex. 2 | 1067 | — | — | 64.1 | — | 100 | 5 | 5.4 | 81 | 16.5 | — | 317 | 167 |
| 14 | Ex. 4 | 879 | — | — | 70.4 | — | 150 | 10 | — | 85 | 11.9 | — | 323 | 41 |
| 15 | Ex. 5 | 855 | — | — | 50.4 | — | 150 | 15 | — | 79 | 4.4 | — | 275 | 69 |
| 16 | OP 1230 | — | — | — | — | — | — | — | — | — | 23.9 | — | 355 | 25 |

Example 1 to 5: Oxa = oxaphospholane (R)Exolit PE 110, Clariant
Example 1 to 5: MeOH = methanol, OctOH = n-octanol, BzOH = benzyl alcohol
Example 4: 31P NMR: in DMSO
Example 8: 154.1 g NaHCO3 in 139.4 g water
Example 9: 112.5 g K2CO3 in 102.3 g water
Example 10: component 3 = aluminum sulfate solution 4.2% Al; component 3 = H2SO4 96%; product: 17.8% P th
Example 11: component 3 = magnesium hydroxide; product: 17.5% P th
Example 12: component 3 = zinc oxide; product: 15.7% P th
Example 13: component 3 = calcium hydroxide; product: 16.7% P th
Example 14: component 3 = zinc oxide; product: 11.9% P th
Example 15: component 3 = magnesium hydroxide; product: 4.4% P th
Example 16: (R)Exolit OP 1230, Clariant
Content: content of target component in product via 31P NMR
Name: Name
Yield: Yield
31 P: prev. shift, 31P NMR
DTA: Differential thermal analysis, °C. for 2% weight loss

TABLE 2

Inventive flame-retardant polymer molding compositions and inventive flame-retardant polymer moldings

| Example | FR from | PS 1 [% by wt.] | PS2 [% by wt.] | PBT [% by wt.] | PA6 [% by wt.] | PA66 [% by wt.] | GF 1 [% by wt.] | MC [% by wt.] | MPP [% by wt.] | ZB [% by wt.] | EP [% by wt.] | EH [% by wt.] | UL94 | Exudation [%] |
|---|---|---|---|---|---|---|---|---|---|---|---|---|---|---|
| 17 | EP 1125960 | 30 | 70 | | | | | | | | | | V-2 | 24 |
| 18 | Ex. 10 | 30 | 70 | | | | | | | | | | V-0 | 4 |
| 19 | Ex. 10 | 23 | 47 | | | | 30 | | | | | | V-0 | 4 |
| 20 | Ex. 10 | 12 | | 52 | | | 30 | 6 | | | | | V-0 | 4 |
| 21 | Ex. 10 | 11.4 | | | 52 | | 30 | | 5.7 | 0.9 | | | V-0 | 8 |
| 22 | Ex. 12 | 20 | | | 50 | | 30 | | | | | | V-0 | 6 |
| 23 | EP 1125960 | 17 | | | | | | | | | 65 | 18 | V-1 | 15 |
| 24 | Ex. 11 | 17 | | | | | | | | | 65 | 18 | V-0 | 6 |

Example 17: 1-Methylimidazolium (2-methoxycarbonylethyl)methylphosphinate

The invention claimed is:

1. A salt of alkyl ester of carboxyethyl(alkyl)phosphinic acid, where the salt has the formula (I)

$R^1$—P(=O)(OX)—$CH_2$—$CH_2$—$CO_2R^2$ wherein $R^1$ and $R^2$ wherein $R^1$ and $R^2$ are identical or different and, independently of one another, are methyl, ethyl, n-propyl, isopropyl, n-butyl, tert-butyl, n-pentyl or a mixture thereof, and X is Mg, Ca, Zn, Sr; Al, Ce, La; Ge, Sn, Pb, Ti, Zr; Sb, Bi; Cr, Mo, W; Mn; Fe, Co or Ni.

2. The salt of alkyl ester of carboxyethyl(alkyl)phosphinic acid, as claimed in claim 1, wherein X is Al, Zn, Ca, Mg, Ti or Ce.

3. A process for the preparation of a salt of alkyl ester of carboxyethyl(alkyl)phosphinic acid, of the formula (I), in which $R^1$, $R^2$ and X are defined as in claim 1, comprising the step of reacting an alkyl ester of carboxyethyl(alkyl)phosphinic acid, of the formula (I), in which $R^1$, $R^2$ are defined as in claim 1, in a solvent system, with a reactant I, wherein reactant I is a compound of an alkali metal, of an element of the second main and transition group, of an element of the third main and transition group, of an element of the fourth main and transition group, of an element of the fifth main and transition group, of an element of the sixth transition group, of an element of the seventh transition group, or of an element of the eighth transition group of the chemical table of elements.

4. A process for the preparation of a salt of alkyl ester of carboxyethyl(alkyl)phosphinic acid, of the formula (I), in which $R^1$, $R^2$ are defined as in claim 1, comprising the steps of reacting an alkali metal salt of alkyl ester of carboxyethyl (alkyl)phosphinic acid, of the formula (I), in which $R^1$, $R^2$ are defined as in claim 1 and X is an alkali metal, in a solvent system, with a reactant II.

5. The process as claimed in claim 4, wherein the reactant II is selected from the group consisting of borates, carbonates, hydroxides, oxides, oxide hydroxides, hydrogencarbonates, hydrogencarbonate hydrates, mixed hydrogencarbonates, mixed hydrogencarbonate hydrates, phosphates, sulfates, sulfate hydrates, hydrogensulfate hydrates, mixed hydrogensulfate hydrates, oxysulfates, acetates, nitrates, fluorides, fluoride hydrates, chloride, chloride hydrates, oxychlorides, bromides, iodides, iodide hydrates, carboxylic acid derivatives, alkoxides and mixtures thereof, wherein the carboxylic acid derivatives or alkoxides are of an element of the second main and transition group, of an element of the third main and transition group, of an element of the fourth main and transition group, of an element of the fifth main and transition group, of an element of the sixth transition group, of an element of the seventh transition group, or of an element of the eighth transition group of the chemical table of elements.

6. A flame retardant comprising a salt of alkyl ester of carboxyethyl(alkyl)phosphinic acid, of the formula (I), as claimed in claim 1, wherein the flame retardant is a flame retardant for clear lacquers, intumescent coatings, wood, and cellulose-containing products.

7. A binder for foundry materials or molding sands comprising a salt of alkyl ester of carboxyethyl(alkyl)phosphinic acid, of the formula (I), as claimed in claim 1.

8. A flame-retardant thermoplastic polymer molding composition comprising from 0.5 to 45% by weight of a salt of alkyl ester of carboxyethyl(alkyl)phosphinic acid, of the formula (I), as claimed in claim 1, and from 0.5 to 99.5% by weight of thermoplastic polymer or a mixture of thermoplastic polymers, where the entirety of the components is 100% by weight.

9. The flame-retardant thermoplastic polymer molding composition as claimed in claim 8, wherein the thermoplastic polymer or mixture thermoplastic polymers are polymers of mono- and diolefins, polymers of cycloolefins or polyesters.

10. A flame-retardant thermoset composition, comprising from 0.1 to 45% by weight of a salt of alkyl ester of carboxyethyl(alkyl)phosphinic acid, of the formula (I), as claimed in claim 1, from 40 to 89.9% by weight of unsaturated polyesters, and from 10 to 60% by weight of vinyl monomer, where the entirety of the components is 100% by weight.

11. A process for the preparation of a flame-retardant polymer molding comprising the steps of mixing the salt of alkyl ester of carboxyethyl(alkyl)phosphinic acid, of the formula (I), according to claim 1, with polymer pellets and optionally with additives to form a mixture, incorporating the mixture in a twin-screw extruder at a temperature of 170° C. (to 280° C., to form a homogenized polymer strand, drawing off the homogenized polymer strand, cooling the homogenized polymer strand in a water bath, pelletizing the homogenized polymer strand and drying the homogenized polymer strand to a residual moisture content of from 0.05 to 5%.

12. A flame-retardant molding composition, comprising from 0.5 to 50% by weight of a salt of alkyl ester of carboxyethyl(alkyl)phosphinic acid, of the formula (I), as claimed in claim 1, from 5 to 99.5% by weight of an epoxy resin, and from 0 to 20% by weight of a hardener, where the entirety of the components is 100% by weight.

13. A flame-retardant polymer molding, polymer film, polymer filament or polymer fiber comprising the flame retardant molding composition of claim 8.

14. A process for the production of a flame-retardant polymer molding comprising the step of processing a flame-retardant molding composition as claimed in claim 8, using an injection-molding machine, at a melt temperature of from 200 to 320° C. to form the polymer molding.

15. A flame retardant article comprising a salt of alkyl ester of carboxyethyl(alkyl)phosphinic acid, of the formula (I), as claimed in claim 1, wherein the flame retardant article is selected from the group consisting of polymer molding compositions, polymer moldings, polymer films, polymer filaments, polymer filaments, polyester and unblended or blended cellulose textiles.

16. A reactive, non-reactive, or both, flame retardant for a polymer comprising a salt of alkyl ester of carboxyethyl (alkyl)phosphinic acid, of the formula (I), as claimed in claim 1.

17. A crosslinking agent or accelerator in the hardening of epoxy resins, of polyurethanes or of unsaturated polyester resins comprising a salt of alkyl ester of carboxyethyl(alkyl) phosphinic acid, of the formula (I), as claimed in claim 1.

18. A polymer stabilizer, light stabilizer, free radical scavenger, heat stabilizer or a combination thereof for cotton textiles, polymer fibers or plastics comprising a salt of alkyl ester of carboxyethyl(alkyl)phosphinic acid, of the formula (I), as claimed in claim 1.

19. A plant protection agent, a plant growth regulator, an herbicide or fungcide comprising a salt of alkyl ester of carboxyethyl(alkyl)phosphinic acid, of the formula (I), as claimed in claim 1.

20. A therapeutic agent for humans or animals comprising a salt of alkyl ester of carboxyethyl(alkyl)phosphinic acid, of the formula (I), as claimed in claim 1.

21. A sequestering agent for the control of deposits in industrial water supply systems, in petroleum production, and in a metal-treatment composition comprising a salt of alkyl ester of carboxyethyl(alkyl)phosphinic acid, of the formula (I), as claimed in claim 1.

22. A petroleum additive comprising a salt of alkyl ester of carboxyethyl(alkyl)phosphinic acid, of the formula (I), as claimed in claim 1.

23. A decolorizer for laundry detergent or cleaning products comprising a salt of alkyl ester of carboxyethyl(alkyl) phosphinic acid, of the formula (I), as claimed in claim 1.

24. An electronics additive comprising a salt of alkyl ester of carboxyethyl(alkyl)phosphinic acid, of the formula (I), as claimed in claim 1.

25. A formaldehyde scavenger in adhesive compositions and moldings comprising a salt of alkyl ester of carboxyethyl (alkyl)phosphinic acid, of the formula (I), as claimed in claim 1.

26. The flame-retardant thermoplastic polymer molding composition as claimed in claim 9, wherein the polymers of mono- and diolefins are selected from the group consisting of polyethylene, polypropylene, polyisobutylene, poly-1-butene, poly-4-methyl-1-pentene, polyisoprene and polybutadiene.

27. The flame-retardant thermoplastic polymer molding composition as claimed in claim 9, wherein polymers of cycloolefins are selected from the group consisting of cyclopentene, norbornene, polyvinyl chloride, polyvinylidene chloride, polyvinyl fluoride, polyvinylidene fluoride, polyacrylates and polymethacrylates, polyacrylamides, polyacrylonitriles, polyvinyl alcohol, polyvinyl acetate, polyalkylene glycols, polyethylene oxide, polypropylene oxide, polyoxymethylene, polyphenylene oxides, polyphenylene sulfides, polyphenylene ether, polyurethanes, polyamides, copolyamides, polyureas, polyimides, polyamideimides, polyetherimides, polyesterimides, polyhydantoins and polybenzimidazoles.

28. The flame-retardant thermoplastic polymer molding composition as claimed in claim 9, wherein the polyesters are polyethylene terephthalate or polybutylene terephthalate.

29. The process according to claim 11, wherein the residual moisture content is 0.1 to 1% by weight.

30. A flame-retardant polymer molding, polymer film, polymer filament or polymer fiber comprising a flame retardant molding composition of claim 10.

31. A flame-retardant polymer molding, polymer film, polymer filament or polymer fiber comprising a flame retardant molding composition of claim 12.

32. A process for the production of a flame-retardant polymer molding comprising the step of processing a mixture as claimed in claim 1, in the form of a flame-retardant molding composition, using an injection-molding machine, at melt temperatures of from 200 to 320° C., to give a polymer molding.

33. A process for the production of a flame-retardant polymer molding comprising the step of processing a flame-retardant molding composition as claimed in claim 12, using an injection-molding machine, at a melt temperature of from 2020 to 320° C., to form the polymer molding.

* * * * *